United States Patent [19]
Utterberg

[11] Patent Number: 5,704,917
[45] Date of Patent: Jan. 6, 1998

[54] NEEDLE STORAGE APPARATUS AND METHOD

[75] Inventor: David S. Utterberg, Seattle, Wash.

[73] Assignee: Medisystems Technology Corporation, Seattle, Wash.

[21] Appl. No.: 538,460

[22] Filed: Oct. 3, 1995

[51] Int. Cl.⁶ .................................................. A61M 5/32
[52] U.S. Cl. ........................... 604/180; 604/174; 604/177; 604/198
[58] Field of Search .......................... 604/162–3, 171, 604/174, 177, 180, 192, 197–9, 263; 128/912, DIG. 26

[56] References Cited

U.S. PATENT DOCUMENTS

| | | | |
|---|---|---|---|
| 4,737,143 | 4/1988 | Russell | 604/174 |
| 4,820,282 | 4/1989 | Hogan | 604/263 |
| 4,994,046 | 2/1991 | Wesson et al. | 604/263 |
| 5,092,461 | 3/1992 | Adam | 604/263 |
| 5,112,311 | 5/1992 | Utterberg et al. | |
| 5,112,313 | 5/1992 | Sallee | 604/180 |
| 5,137,519 | 8/1992 | Littrell et al. | 604/174 |
| 5,350,368 | 9/1994 | Shields | 604/177 |
| 5,433,703 | 7/1995 | Utterberg et al. | 604/177 |
| 5,584,813 | 12/1996 | Livingston et al. | 604/177 |

OTHER PUBLICATIONS

Data Sheet by Sherwood Medical entitled "Angel Wing" Safety Needle System Blood Collection Set, Monoject, 2 Pages, Printed in U.S.A. 1995.

Primary Examiner—Michael Powell Buiz
Assistant Examiner—Bhisma Mehta
Attorney, Agent, or Firm—Gerstman, Ellis & McMillin, Ltd.

[57] ABSTRACT

A hollow guard having a wall for receiving and enclosing a medical needle after use. The guard has an open end to allow a needle to be inserted into the guard. An adhesive member has a section typically permanently attached to the wall, with portions of the adhesive member being spaced from the wall, for temporary attachment to a patient's skin to secure the guard on the patient's skin.

12 Claims, 2 Drawing Sheets

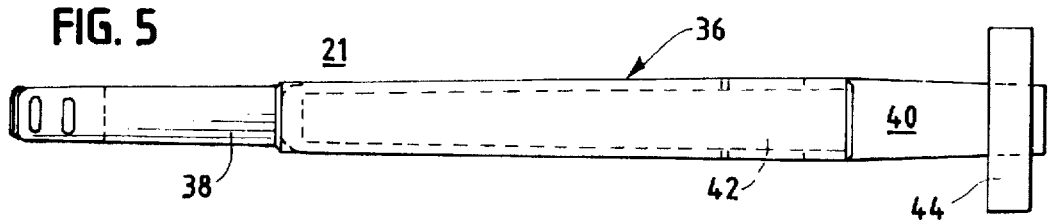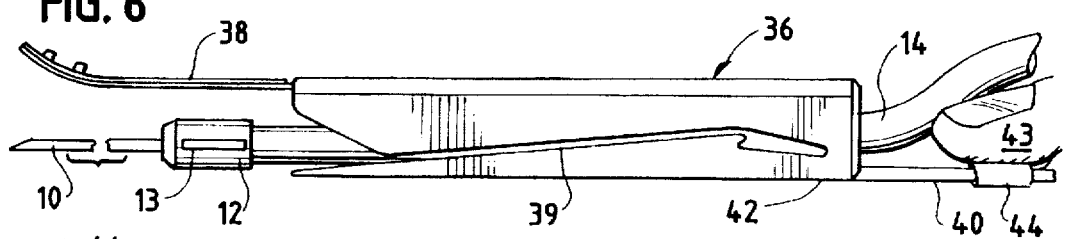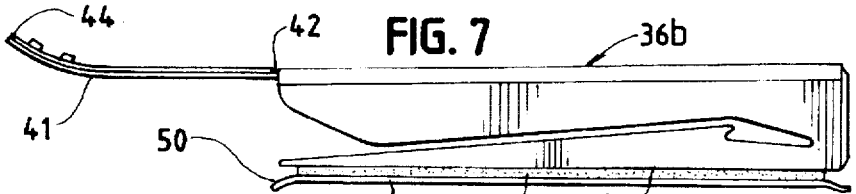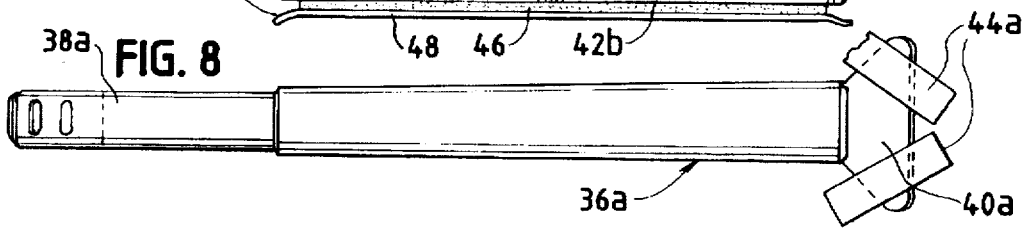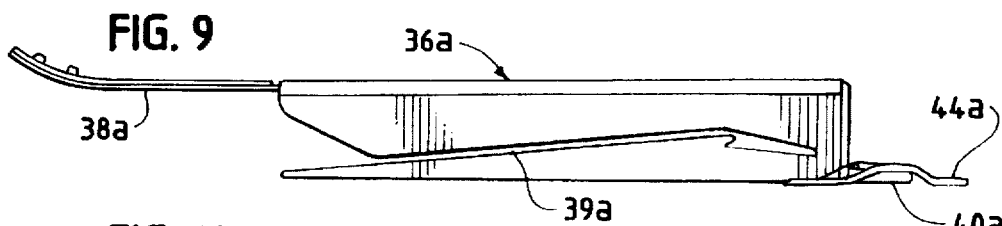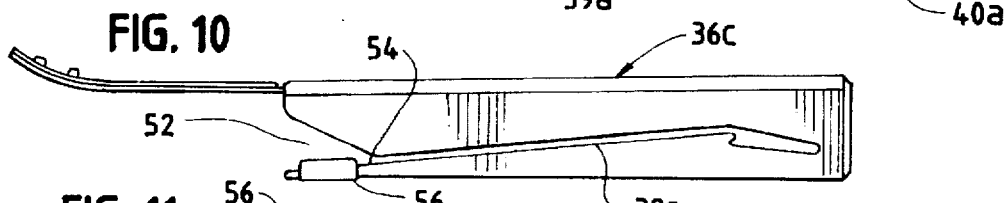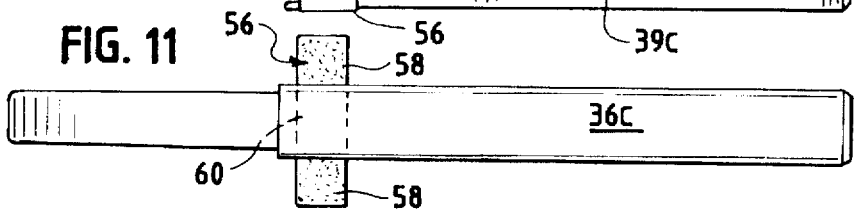

NEEDLE STORAGE APPARATUS AND METHOD

BACKGROUND OF THE INVENTION

In Utterberg U.S. Pat. No. 5,112,311 a guard or storage apparatus for a winged intravascular (I.V.) needle and hub assembly is disclosed, in which the needle guard is a hollow, generally tubular structure which is typically placed behind a needle emplaced in a blood vessel of a patient, with the guard surrounding the connecting tube of the needle. Then, to withdraw the needle from the patient, the above cited patent teaches the step of manually pressing an "anchor" which extends forwardly from the hollow guard. The needle may then be withdrawn from the patient so that it slides into the stationary, hollow guard, with the wings of the needle hub sliding through a pair of opposed slots in the guard. The guard than locks the needle in the enclosed position inside of the guard, so that the assembly may be handled without danger of injury from the needle point, which is stored in a position recessed within the guard.

As the above technique is accomplished, the hand which is pressing against the anchor of the hollow guard is in a position forward of the needle as the needle is retracted into the guard. While that is basically safe under the specific conditions of operation, it would be desirable to provide a system operated by one hand, where neither hand has to operate the guard from a position in front of the needle until after the needle has been completely enclosed within the hollow needle guard. Also, it is desirable to provide a system in which I.V. needles can be safely withdrawn from engagement with the patient into a hollow guard in those circumstances where the hollow guard does not carry a forward projecting anchor.

By this invention, the above objectives can be achieved.

DESCRIPTION OF THE INVENTION

In accordance with this invention, a hollow guard is provided having a sidewall for receiving and enclosing a medical needle after its use for supplying medicament or blood to a patient. The guard has an open end to allow a needle to be inserted into the guard. The guard also has a longitudinal axis, and an adhesive member having a section which is permanently attached to the sidewall. The adhesive member may be adhesive tape.

Portions of the adhesive member may be spaced from the sidewall, and may be temporarily attached to a patient's skin to secure the guard on the patient's skin.

Preferably, the section of the tape which is attached to the sidewall is permanently attached thereto, typically with a first, permanent adhesive for securing the tape section to the sidewall. The spaced tape sections may carry a second adhesive, typically of different formulation from the first adhesive, suitable for temporary, releasable contact with the skin.

It is also preferred for the tape to have adhesive layer portions spaced from the guard which are covered by a removable, protective sheet of generally conventional design to protect the adhesive layers thereof until they are removed for use.

The section of the adhesive tape which is preferably permanently attached to the hollow guard is also preferably located centrally along the length of the tape, to provide tape portions on opposed sides of the guard for the best temporary skin attachment. Also, the sidewall preferably defines a pair of opposed slots for slidingly receiving wings of a needle hub as the needle is inserted into the guard.

One may remove a medical needle from a patient by placing the hollow guard onto the skin of a patient adjacent the needle, and applying an adhesive member positioned transversely across the hollow guard to the skin of a patient, to temporarily secure the guard on the patient's skin. One then inserts the needle into the hollow guard while withdrawing the needle from the skin and preferably removing the hollow guard from the skin with the needle inside the guard. By this invention, this can be accomplished in a manual manner without placing a hand in front of the needle until the needle is safely secured inside of the guard.

DESCRIPTION OF DRAWINGS

In the drawings.

FIG. 5 is a plan view of another embodiment of hollow tubular needle guard of this invention, shown to be positioned on the patient;

FIG. 6 is an elevational view of the needle guard of FIG. 5, showing the needle in the process of being removed and sliding into the guard while the guard is being manually retained in position on the patient's skin;

FIG. 7 is a plan view of another embodiment of the needle guard of this invention shown positioned on the patient's skin;

FIG. 8 is a plan view of another embodiment of the needle guard;

FIG. 9 is an elevational view of the needle guard of FIG. 8;

FIG. 10 is an elevational view of another embodiment of the needle guard of this invention, shown to be carrying a length of adhesive tape from a lower jaw portion of the slot forward opening; and FIG. 11 is a plan view of the embodiment of FIG. 10.

DESCRIPTION OF SPECIFIC EMBODIMENTS

Figure 1:
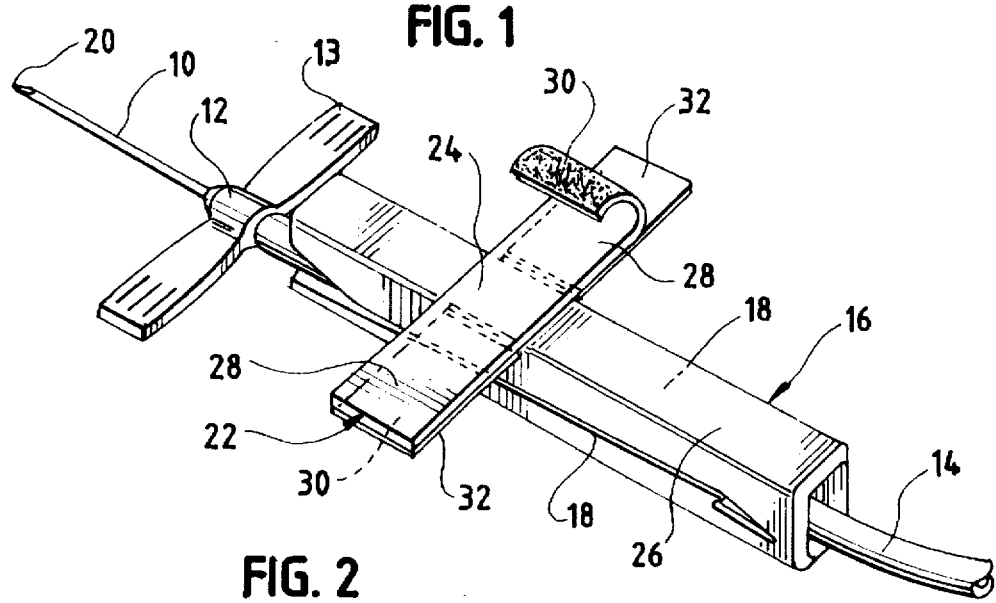
FIG. 1 is a perspective view of a hollow, substantially tubular needle guard of this invention, shown threaded onto IV tubing and positioned behind an IV needle.
Figure 2:
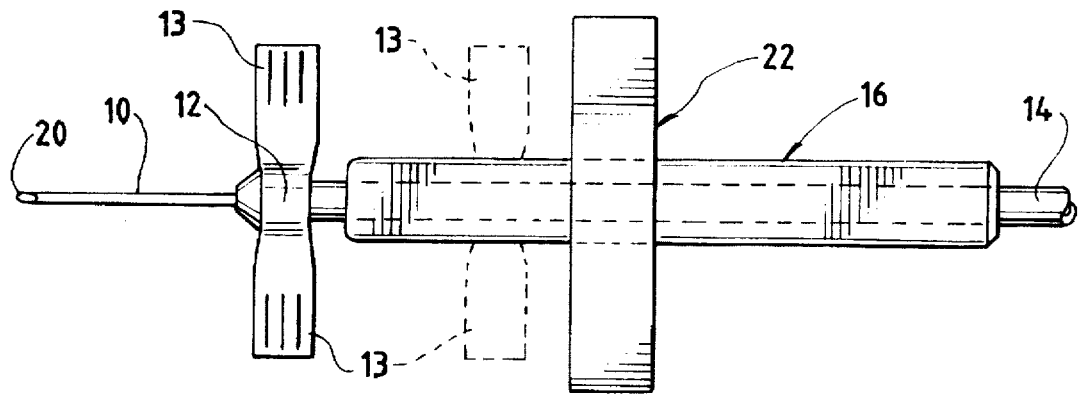
FIG. 2 is a plan view of the guard and needle assembly of FIG. 1.
Figure 3:
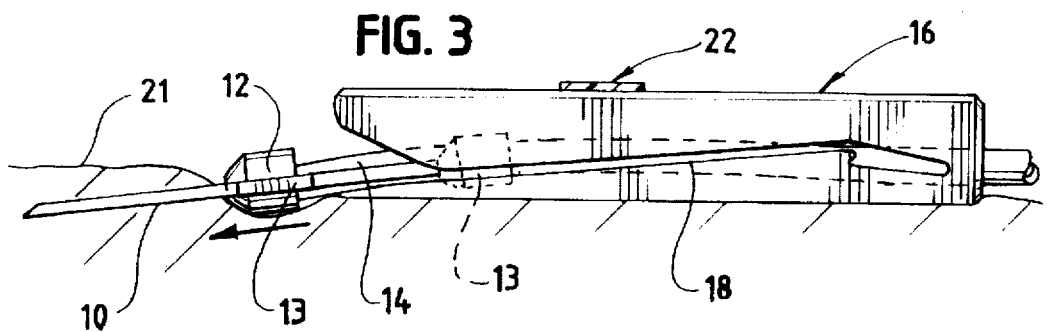
FIG. 3 is an elevational view, with a portion broken away, showing the needle and guard assembly with the needle emplaced through the skin of a patient for IV administration, or for blood transport as in the case of a hemodialysis fistula needle.
Figure 4:
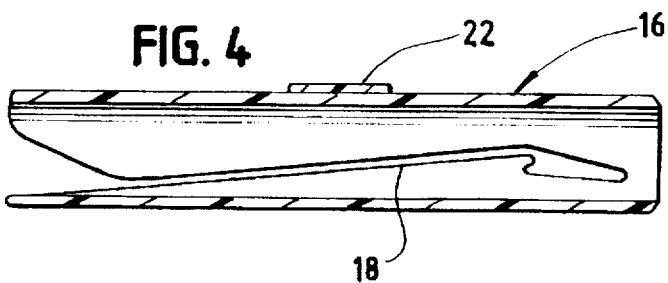
FIG. 4 is a longitudinal sectional view of the hollow guard of this invention.

Referring to FIGS. 1 through 4, a fistula needle 10 having a hub 12 with wings 13 is shown as a conventional design, attached to a length of flexible tubing 14 and carrying a needle sheath 16, which is in the form of a hollow tube through which the tubing 14 extends. Such a fistula needle is conventionally used in hemodialysis procedures, while similar needles are also used in a large variety of other medical procedures.

Tubular housing 16 may be of a conventional design, having slots 18 on opposed wall portions of sheath 16 for receiving the wings 13 of needle and hub 10, 12 as the needle is retracted into sheath 16, to safely enclose the point 20 of the needle.

As is conventionally practiced and disclosed in the previously cited Utterberg patent, when it is desired to withdraw needle 10 from the skin 21, sheath 16 is secured in position by manually holding or pressing a forwardly projecting "anchor" of the type shown in the previously cited patent. Then, one may pull on tubing 14 to cause needle 10 to withdraw from the skin, and the entire assemblage 10, 12 to slide back into sheath 16, with wings 13 extending outwardly through slots 18, as shown particularly in FIGS. 2 and 3 in dotted lines.

In accordance with this invention, to facilitate the above process, said hollow guard or sheath 16 carries a length of adhesive tape 22 having a first section 24 which is permanently attached to upper wall 26 of sheath or guard 16. This permanent attachment may be accomplished by the use of a permanent adhesive such as epoxy or the like, being coated on adhesive member 22 in area 24. Adhesive member 22 is typically a piece of adhesive tape, bonded at first, central section in permanent manner to sheath or guard 16.

The outer portions 28 of adhesive tape 22 are shown in FIG. 1 to extend substantially laterally from hollow guard 16, to be spaced from the wall 26 thereof, and extending transversely to the axis of the guard 16, which extends substantially in the direction of needle 10 as shown.

The respective, spaced adhesive tape portions 28 may be coated with a temporary, medically acceptable adhesive 30 of known type for temporary attachment of adhesive tape 22 to the patient's skin. Thus, when this is accomplished, sheath 16 is held in position on the patient's skin in the desired location without any need for manual retention of it. Also, each of the temporary adhesive layer portions 30 may be conventionally covered by a removable protective sheet 32 in the normal manner for adhesive bandages, to preserve the temporary adhesive layers 30 until they are to be used.

Hollow guard 16 thus may be manufactured with adhesive tape 22 permanently attached to it and extending laterally across the guard 16. Removable, protective sheets 32 may then be removed from the outwardly projecting portions of tape 22, and used to secure guard 16 to the skin in a desired location on the patient during a dialysis or other procedure. Through most of the dialysis procedure, this desired position may be substantially spaced from needle and hub 10, 12, but with guard 16 being threaded on tube 14. Then, at the end of dialysis, the tape portions 28 may be removed from the skin; the guard advanced to the desired position shown, and the guard 16 being retaped with the same tape to the skin again. Then, needle 10 can be withdrawn from the skin, entering into guard 16, with the use of only one hand to pull tube 14 until the needle point 20 is recessed within the guard, for protection of all who handle it.

Thus, a guard without a forward "anchor" may be safely used.

However, referring to FIGS. 5 and 6, another hollow guard or sheath 36 is shown, being basically similar to the guard of FIGS. 1-4 except as otherwise indicated herein.

FIG. 6 shows the same needle and hub system 10, 12, having wings 13, and with guard 36 carried in surrounding relation to tube 14.

In this embodiment, an overlying flap 38 extends forwardly from the needle-facing end of guard 36 to overlie at least a portion of needle 10 prior to withdrawing of said needle into the hollow guard. Flap 38 can thus provide added protection to the user against being accidentally stuck by needle 10 as it is being withdrawn, since the flap serves as an overlying barrier to shield the needle point from contact with hands or the like that may be in the vicinity as the needle is being withdrawn. Such a flap may be used on any of the needle guards disclosed by this invention.

Also, in this embodiment, hollow, tubular guard 36 defines a rearwardly projecting anchor member 40 extending rearwardly from the bottom wall 42 of the tubular guard. The presence of rearwardly projecting member 40 permits manual or other retention or pressing by means of a finger 43, a transverse piece of tape 44 or the like, or both as shown in FIGS. 5 and 6. Thus, the hollow guard may be held in position by the rearwardly projecting anchor 40, to hold hollow guard 36 in position on the skin 21 as the needle 10 is being withdrawn into the hollow guard.

FIGS. 8 and 9 show a slightly modified hollow guard 36a, which is of substantially similar design to hollow guard 36, having forwardly extending flap 38a from the top wall, a pair of slots 39a on opposed walls, of similar design to the previous embodiment, and a rearwardly projecting anchor member 40a, which is shown to be of truncated triangular shape, with sides thereof extending laterally outwardly from the balance of tubular guard 36a, to facilitate attachment by adhesive tape lengths 44a.

Alternatively, for the embodiments of FIGS. 5 through 9, the lengths of adhesive tape 44, 44a may have a central portion that is permanently adhered to rearwardly projecting anchor 40 or 40a, with end portions that project outwardly from the anchor being coated with a temporary, skin-compatible adhesive in a manner similar to that discussed in FIG. 1. Removable cover layers may be applied to the temporary adhesive portions on the end sections of the tape lengths 44, 44a, to be removed when guard 36 or 36a is to be placed on the patient. Thus, the guard is temporarily secured to the patient to permit one handed withdrawal of needle 10 in the manner previously described. The adhesive members 40, 40a may be permanently secured to the guard, which greatly facilitates the convenience of the procedure.

Referring to FIG. 7, another embodiment of the guard of this invention is shown, in which guard 36b is of similar structure to guards 36, 36a except that it carries no rearwardly projecting anchor member. The bottom wall 42b carries, in this embodiment, a length of double sided adhesive tape 46, extending along most of the length of bottom wall 42b from end to end of guard 36b. Thus, tape 46 adheres firmly and permanently to bottom wall 42b, and displays an underside 48 which also carries a temporary skin adhesive. Removable release liner 50 may be peeled off of the bottom adhesive layer 48, so that guard 36b may be adhered in removable manner to the skin of a patient in the desired position, so that one handed needle withdrawal can take place without necessarily touching guard 36b, as in the previous embodiments.

However, if desired, flap 41, used as a shield against needle 10 as previously described, may define a transverse line of bending weakness 42, so that one may manually bend flap 41 downwardly with a finger pressing adjacent its outer end 44, to press a gauze pad that conventionally overlies the skin entry site for needle 10. Thus, flap 40 in this instance is being used as an anchor in a manner similar to that described in the previously cited patent, which at the same time flap 40 provides protection to that finger which is pressing the needle entry site as the needle is withdrawn. This pressure is desirable to minimize bleeding after withdrawal of the needle.

Referring to FIGS. 10 and 11, hollow guard 36c may be of identical design to the previous hollow guard 36b except for the manner in which adhesive retention is accomplished.

In this embodiment, as in the previous embodiments, the opposed slots 39 c define a relatively wide slot end portion 52 adjacent the forward, needle-facing end of guard 36c. A lower surface of widened slot end portion carries an adhesive member 56 (typically adhesive tape) which extends laterally beyond the width of hollow guard 36c, as particularly shown in FIG. 11. Thus, outer portions 58 of the adhesive member or tape can temporarily stick to the patient in the manner of typical tape, for retention of the hollow guard. The central portion 60 of adhesive member 56 may be attached by a permanent adhesive to the lower surface or "jaw" area 54. Removable release sheets may be provided to the adhesive of areas 58 as desired, to provide a product that is ready to use without the need to find and apply adhesive tape to it.

The above has been offered for illustrative purposes only and is not intended to limit the scope of the invention of this application, which is as defined in the claims below.

That which is claimed is:

1. A hollow guard having a wall for receiving and enclosing a medical needle after use, said guard having an open end to allow a needle to be inserted into said guard, said guard having a central longitudinal axis, and an adhesive tape having a section permanently attached to said wall with the adhesive tape extending transversely to said axis, whereby portions of said adhesive tape are spaced from said wall and may be temporarily attached to the patient's skin to secure said guard on the patient's skin, said spaced portions of said tape having adhesive layer portions that are covered by a removable, protective sheet, said attached section of the adhesive tape being located centrally along said length of tape to provide said tape portions on opposed sides of the guard for temporary skin attachment.

2. The hollow guard of claim 1, said guard having an open, forward, needle-facing end, to allow a needle to be inserted into said guard, in which said guard defines a pair of opposed slots for slidingly receiving wings of a needle hub as the needle is inserted into the guard, said slots defining a relatively wide slot end portion adjacent the forward, needle-facing end of said hollow guard, a lower surface portion of said widened slot end portion carrying an adhesive tape which extends laterally beyond the width of said hollow guard, whereby outer portions of said adhesive tape can temporarily stick to the patient for retention of said hollow guard.

3. The hollow guard of claim 2 in which portions of said adhesive member which extend beyond the width of said hollow guard are covered by a removable release liner for protection of said adhesive member until used.

4. The hollow guard of claim 1 in which said wall comprises opposed sidewall portions which define a pair of opposed slots for slidingly receiving wings of a needle hub as a needle is inserted into the guard.

5. The hollow guard of claim 1 in which said adhesive tape has a first, permanent adhesive securing said permanently attached section to said wall, and the spaced portions carry a second adhesive of different formulation from the first adhesive, suitable for temporary, releasable contact with the skin.

6. A hollow guard having a wall for receiving and enclosing a medical needle after use, said guard having an open end to allow a needle to be inserted into said guard and an adhesive member permanently attached to said wall by a first adhesive, at least portions of said adhesive member carrying a second adhesive permitting temporary attachment to a patient's skin to secure said guard upon the patient's skin, said guard having a needle-facing end an opposed end, and a bottom wall said hollow guard defining a rearwardly projecting anchor member extending rearward from said bottom wall and proportioned to permit retention of said rearwardly projecting anchor member to hold the hollow guard in position on the skin as the needle is being withdrawn into said hollow guard.

7. The hollow guard of claim 6 in which said second, temporary adhesive on said adhesive member is covered by at least one removable, protective sheet.

8. The hollow guard of claim 7 in which said wall defines a pair of opposed slits for slidingly receiving wings of a needle hub as a needle is inserted into the guard.

9. The hollow guard of claim 8 in which said first permanent adhesive and said second temporary adhesive are of different formulations.

10. The hollow guard of claim 6 which defines a top wall, and a flap extending forwardly from a needle-facing hollow guard end and the top wall to overlie at least a portion of a needle prior to withdrawing the needle into the hollow guard.

11. A hollow guard having a wall for receiving and enclosing a medical needle after use, said guard having an open end to allow a needle to be inserted into said guard, said hollow guard having a needle-facing end, an opposed end, and a bottom wall; said hollow guard defining a rearwardly projecting anchor member extending rearwardly from said bottom wall and proportioned to permit pressing of said rearwardly projecting anchor member to hold manually the hollow guard in position on the skin as the needle is being withdrawn into said hollow guard.

12. The hollow guard of claim 11 which defines a top wall, and a flap extending forwardly from the needle facing end and the top wall to overlie at least a portion of a needle prior to withdrawing the needle into the hollow guard.

* * * * *